United States Patent [19]
Basoglu et al.

[11] Patent Number: 5,910,117
[45] Date of Patent: Jun. 8, 1999

[54] REAL TIME COLOR DOPPLER ULTRASOUND IMAGING

[76] Inventors: Christopher H. Basoglu, 21832—2nd Ave. W., Bothell, Wash. 98021; Yongmin Kim, 4431 NE. 189th Pl., Seattle, Wash. 98195

[21] Appl. No.: 09/027,112

[22] Filed: Feb. 18, 1998

Related U.S. Application Data

[60] Provisional application No. 60/038,666, Feb. 20, 1997.

[51] Int. Cl.$^6$ .................................................. A61B 8/00

[52] U.S. Cl. .......................... 600/454; 600/455; 600/456

[58] Field of Search .................................. 600/437, 441, 600/442, 443, 454, 455, 456

[56] References Cited

U.S. PATENT DOCUMENTS

| | | | |
|---|---|---|---|
| 5,375,600 | 12/1994 | Melton, Jr. et al. | 600/455 |
| 5,415,171 | 5/1995 | Goh et al. | 600/443 |
| 5,505,204 | 4/1996 | Picot et al. | 600/456 |

*Primary Examiner*—Francis J. Jaworski
*Assistant Examiner*—Ali M. Imam
*Attorney, Agent, or Firm*—Steven P. Koda

[57] ABSTRACT

A method for generating color Doppler images is implemented in real time using digital processing steps implemented on multi-purpose microprocessors. Processing is reduced by estimating velocity only when a tissue threshold decision for a given sample indicates that the sample is not tissue. Arc tangent calculations in the velocity estimation are performed using simplified look-up tables without sacrificing accuracy. One look-up table is linerally quantized. A second is nonlinearly quantized.

5 Claims, 14 Drawing Sheets

| CYCLES | MULTIPLY UNIT | ADD/SUBTRACT UNIT | LOAD/STORE UNIT | BRANCH UNIT |
|---|---|---|---|---|
| 1 | | | LD$_1$ | |
| 2 | | | LD$_2$ | |
| 3 | | A$_1$ | LD$_3$ | |
| 4 | | A$_2$ | LD$_4$ | B$_1$ |
| 5 | | A$_3$ | LD$_5$ | B$_2$ |
| 6 | | A$_4$ | LD$_6$ | |
| 7 | | A$_5$ | LD$_7$ | |
| 8 | | A$_6$ | LD$_8$ | |
| 9 | | A$_7$ | LD$_{10}$ | |
| 10 | M$_1$ | A$_8$ | LD$_{11}$ | |
| 11 | M$_2$ | | LD$_9$ | |
| 12 | M$_3$ | | LD$_1$ | |
| 13 | M$_4$ | A$_9$ | LD$_2$ | |
| 14 | | A$_{10}$ | LD$_{12}$ | |
| 15 | M$_5$ | A$_{12}$ | LD$_3$ | |
| 16 | | A$_{11}$ | S$_1$ | |
| 17 | | | S$_2$ | |
| 18 | | | LD$_4$ | |
| 19 | | A$_1$ | LD$_{13}$ | |
| 20 | | A$_2$ | S$_3$ | B$_1$ |
| 21 | | A$_3$ | LD$_5$ | B$_2$ |
| 22 | | A$_4$ | LD$_6$ | |
| 23 | | A$_5$ | LD$_7$ | |
| 24 | | A$_6$ | LD$_8$ | |
| 25 | | A$_7$ | LD$_{10}$ | |
| 26 | M$_1$ | A$_8$ | LD$_{11}$ | |
| 27 | M$_2$ | | LD$_9$ | |
| 28 | M$_3$ | | LD$_1$ | |
| 29 | M$_4$ | A$_9$ | LD$_2$ | |
| 30 | | A$_{10}$ | LD$_{12}$ | |
| 31 | M$_5$ | A$_{12}$ | LD$_3$ | |
| 32 | | A$_{11}$ | S$_1$ | |
| 33 | | | S$_2$ | |
| 34 | | | LD$_4$ | |

FIG. 13

| CYCLES | MULTIPLY UNIT | ADD/SUBTRACT UNIT | LOAD/STORE UNIT #1 | LOAD/STORE UNIT #2 | BRANCH UNIT |
|---|---|---|---|---|---|
| 1 | | | $LD_1$ | $LD_2$ | |
| 2 | | $A_1$ | $LD_3$ | $LD_4$ | |
| 3 | | $A_2$ | $LD_{11}$ | | $B_1$ |
| 4 | | $A_3$ | | | $B_2$ |
| 5 | | $A_4$ | $LD_5$ | | |
| 6 | | $A_5$ | $LD_6$ | | |
| 7 | | $A_6$ | $LD_7$ | $LD_8$ | |
| 8 | | $A_7$ | $LD_{10}$ | | |
| 9 | $M_1$ | $A_8$ | | | |
| 10 | $M_2$ | | $LD_9$ | | |
| 11 | $M_3$ | | | | |
| 12 | $M_4$ | $A_9$ | | | |
| 13 | | $A_{10}$ | $LD_1$ | $LD_2$ | |
| 14 | | $A_1$ | $LD_3$ | $LD_4$ | |
| 15 | | $A_2$ | $LD_{11}$ | $LD_{12}$ | $B_1$ |
| 16 | $M_5$ | $A_3$ | $S_1$ | | $B_2$ |
| 17 | | $A_{11}$ | $LD_5$ | | |
| 18 | | $A_{12}$ | $LD_6$ | | |
| 19 | | $A_4$ | $LD_7$ | $LD_8$ | |
| 20 | | $A_5$ | $LD_{10}$ | $S_2$ | |
| 21 | $M_1$ | $A_6$ | $LD_{13}$ | | |
| 22 | $M_2$ | $A_7$ | $LD_9$ | $S_3$ | |
| 23 | $M_3$ | $A_8$ | | | |
| 24 | $M_4$ | $A_9$ | | | |

FIG. 14

| CYCLES | MULTIPLY UNIT | ADD/SUBTRACT UNIT#1 | ADD/SUBTRACT UNIT#2 | LOAD/STORE UNIT#1 | LOAD/STORE UNIT#2 | BRANCH UNIT |
|---|---|---|---|---|---|---|
| 1 | | | | LD$_1$ | LD$_2$' | |
| 2 | | A$_1$ | A$_2$ | LD$_3$' | LD$_4$' | |
| 3 | | A$_3$ | A$_4$ | LD$_{11}$ | | B$_1$' |
| 4 | | A$_5$ | A$_6$ | LD$_5$' | LD$_6$ | B$_2$' |
| 5 | | A$_7$ | | LD$_7$' | LD$_8$ | |
| 6 | M$_1$ | A$_8$ | | LD$_{10}$ | LD$_1$ | |
| 7 | M$_2$ | | | LD$_9$ | LD$_2$ | |
| 8 | M$_3$ | A$_1$ | A$_2$ | LD$_3$ | LD$_4$ | |
| 9 | M$_4$ | A$_3$ | A$_4$ | S$_1$ | LD$_{12}$ | B$_1$ |
| 10 | | A$_5$ | A$_6$ | LD$_5$ | LD$_6$ | B$_2$ |
| 11 | M$_5$ | A$_7$ | A$_9$' | LD$_7$ | LD$_8$ | |
| 12 | M$_1$ | A$_8$ | A$_{10}$' | LD$_{10}$ | =LD$_1$= | |
| 13 | M$_2$ | A$_{11}$' | A$_{12}$' | LD$_9$ | =LD$_2$= | |
| 14 | M$_3$ | =A$_1$= | =A$_2$= | S$_2$ | =LD$_3$= | |
| 15 | | | | LD$_{13}$ | =LD$_4$= | |
| 16 | | | | S$_3$' | LD$_{11}$ | |

FIG. 15

| | COLOR TO COLOR | COLOR TO GRAY | COLOR TO ZERO | GRAY TO COLOR | GRAY TO GRAY | GRAY TO ZERO | ZERO TO COLOR | ZERO TO GRAY | ZERO TO ZERO |
|---|---|---|---|---|---|---|---|---|---|
| NUMBER OF CYCLES | 21 | 9 | 9 | 22 | 3 | 7 | 22 | 7 | 3 |

FIG. 16

REAL TIME COLOR DOPPLER ULTRASOUND IMAGING

CROSS REFERENCE TO RELATED APPLICATIONS

This invention is related to U.S. Provisional Patent Application Ser. No. 60/038,666 filed Feb. 20, 1997 for Real-Time Algorithm for Generating Color Doppler Ultrasound Images on Commercially Available Microprocessors.

BACKGROUND OF THE INVENTION

This invention relates to ultrasound imaging methods and apparatus, and more particularly to color doppler imaging methods and apparatus.

Medical imaging systems are used as diagnostic tools for viewing internal areas of a patient's body. Imaging systems based on ultrasound technology are desirable because such systems are non-invasive, portable and generally easy to use. Ultrasound energy is sound wave energy having a frequency greater than approximately 20 kHz. To generate ultrasound energy, electronic signals are input to a transducer which converts the electrical signals into ultrasound signals. Ultrasound signals, typically of 2 MHz to 10 MHz, are transmitted into a patient's body where they are in-part absorbed, dispersed, refracted and reflected. Reflected ultrasound signals are received at transducer elements which convert the reflected ultrasound signals back into electronic echo signals. The echo signals undergo beamforming to correlate the ultrasound signals. Subsequently the beam-formed signals are processed to analyze echo, Doppler, and flow information and obtain an image of the patient's targeted anatomy (e.g., tissue, fetus, vessels, blood flow).

Individual images produced by ultrasound imaging systems include discrete frames. Each frame has a limited field of view due to a relatively narrow region traversed by the transmitted ultrasound energy. As the transducer probe is manipulated along the patient's body surface, each previous image is replaced on the viewing display by a new image defined by the current position, and thus field of view, of the transducer probe. The data for generating one output image frame typically may be acquired in 20 to 200 milliseconds, depending on the desired target depth and the amount of data to be collected. To perform imaging in real time, the combined time for processing and displaying image data is not to be longer than the time spent in acquiring the data.

A B-mode image is a brightness image in which component pixels are brightened in proportion to a corresponding echo signal strength. The brightness image represents a two dimensional cross section of a patient target area through a transducer's scanning plane. Typically the B-mode image is a gray scale image in which the range of darker to brighter gray-scale shades corresponds to increasing brightness or echo strength. The typical ultrasound B-mode image is formed by a linear scan or sector scan of the patient's target area with the transducer probe.

Velocities of moving targets within the area scanned are measured by performing Doppler analysis on the gathered data. Blood flow, for example, may be calculated throughout a given image plane and displayed as a color overlay on a B-mode image. The resulting image is referred to as a BC-mode image. Typically, a large number of complex operations, such as arctangent, division, and square root operations are required for each output pixel of a BC-mode image. As a result, color Doppler imaging has not been performed in real time on general-purpose microprocessors without sacrificing functionality or accuracy.

Following is background on conventional color Doppler processing:

Color Doppler input Data

Input data is generated by emitting, then receiving, ultrasound signals at a transducer. The signals are modulated on a specific carrier frequency ($w_c$). The amount of energy transmitted over time to a specific location is:

$$T(t)=2\cos(w_c t)=e^{jw_c t}+e^{-jw_c t}$$

Such energy is transmitted to many points within the body. Echo data samples are received in both a time range and a spatial range. The number of samples taken per spatial location over time typically is small (e.g., not more than 16). A set of data samples from a specific spatial location over time is called an ensemble.

The instantaneous energy of a received ensemble (R(t)), depends on the acoustic reflectance, B(t), of the tissue being scanned. The frequency of the received ensemble is a combination of the carrier frequency, $w_c$, and any Doppler frequency, $w_d$, that is present. The energy of the received ensemble is:

$$R(t)=B(t)*[e^{j(w_c-w_d)t}+e^{-j(w_c-w_d)t}]$$

The carrier frequency is removed from the ensemble using quadrature down conversion as follows:

$$LPF[B(t)e^{jw_c t}]=LPF[B(t)(e^{j(2w_c-w_d)t}+e^{jw_d t})]=B(t)*e^{jw_d t}$$

where LPF signifies a low pass filter. To remove the dc components in B(t) (which represent tissue) each ensemble is passed through a high pass filter. The resulting complex samples are:

$$HPF[B(t)*e^{jw_d t}]=P(t)*e^{jw_d t}=I(t)+jQ(t)$$

where P(t) is the power of the received Doppler signal, I(t) is the real component of $P(t)e^{jw_d t}$, and Q(t) is the imaginary component of $P(t)e^{jw_d t}$.

Deriving the Doppler Frequency

One method for calculating Doppler frequency is to use Fast Fourier Transforms (FFT) to convert each ensemble into the frequency domain, then locate the small peak in the FFT spectrum. This peak corresponds, for example, to the Doppler signal from moving blood. The use of FFTs, however, can lead to inaccuracies. This is because the FFT treats the ensemble as being periodic. Since this is not generally the case, the periodicity assumption causes a discontinuity in the results which is not part of the original ensemble. To ameliorate this, it is known to use a window function. However, in doing so, the frequency domain resolution suffers. Accordingly, time domain techniques have been developed in the art.

A common time domain method estimates the Doppler frequency by computing a mean frequency of the ensemble using an autocorrelation algorithm. To compute the autocorrelation function, the jth point in the output signal is the sum of the products of the input signal and the complex conjugate of the input signal shifted right by j points. The value j ranges from 0 to J−1. The first lag of the autocorrelation function is where j equals 1. The product terms for the first lag are:

$$L_h=(I_h I_{h-1}+Q_h Q_{h-1})+j(Q_h I_{h-1}-Q_{h-1}I_h)$$

where h is an index into the ensemble. The instantaneous frequency of the ensemble is calculated as the instantaneous change in phase, as follows:

phase=$\Delta\Phi_h$=full arctan $(Q_h/I_h)$, and $\Delta\Phi_h - \Delta\Phi_{h-1}$ = full arctan $(Q_h/I_h)$-full arctan $(Q_{h-1}/I_{h-1})$ with $\Delta\Phi_h - \Delta\Phi_{h-1}$ = full arctan $[(Q_hI_{h-1} - Q_{h-1}I_h)/(I_hI_{h-1} + Q_hQ_{h-1})]$ where full arctan returns a value from -pi to pi. The numerator in the above full arctan equation is the imaginary part of the product terms of the first lag autocorrelation of the ensemble. The denominator of the same equation is the real part of the product terms of the first lag autocorrelation of the ensemble. The mean frequency of the ensemble is proportional to the phase of the mean output sample of the first lag as follows:

$$\overline{\Delta\Phi} = \text{full arctan}\frac{\sum_{h=0}^{E-1} Q_hI_{h-1} - Q_{h-1}I_h}{\sum_{h=0}^{E-1} I_hI_{h-1} + Q_hQ_{h-1}} = \text{full arctan}\frac{\text{num}}{\text{denom}}$$

where E is the number of the complex samples per ensemble. The numerator of this equation is herein referred to as 'num,' while the denominator is referred to as 'denom.'

Generating Color Velocity Images

To estimate blood flow velocities, the complex outputs of the autocorrelation function are converted into velocities, as follows:

estimated velocity=[atan2(num,denom)]/$\pi$ where atan2(num,denom) returns the phase of (denom+j num) from $-\pi$ to $\pi$ in the complex plane. The $\pi$ in the denominator normalizes the output from -1 to 1. Alternatively, the function $\theta$=arctan[abs(num)/abs(denom)] is used, which returns the phase of (denom+j num) from 0 to $\pi/2$ in the complex plane.

The estimated velocity equation is applied to every num-denom pair in each ensemble so that an entire range of velocities is generated. These velocities are then quantized into a small number of bits. In a 5 bit quantization, for example, each velocity is mapped to one of 32 different colors. Note that the equation is implemented even for data pairs which correspond to tissue rather than blood flow.

Once the velocities are calculated, a color Doppler image is generated conventionally by overlaying the velocity image on top of the corresponding gray-scale tissue image. This process includes a pixel-by-pixel decision of whether to output an estimated velocity value or a gray-scale tissue value. Each incoming echo (tissue) pixel is checked against a predetermined tissue threshold value. If the tissue value is greater that the tissue threshold value, it is a valid tissue pixel. Thus, the tissue value is used in the output image. If the tissue value is less than the tissue threshold value, and a color flow velocity test is passed, then the color flow value is used in the output image. The color flow validity test determines whether the magnitude $(\text{num}^2+\text{denom}^2)^{0.5}$ and the estimated velocity exceed their respective thresholds. If a pixel fails this validity test, then the tissue value is used in the output image, even though the tissue value is less than the tissue threshold value.

The complexity of these algorithms has presented a challenge to implementing color Doppler imaging in real time using general purpose processors. Conventionally, functionality or accuracy is compromised to achieve real-time performance. Alternatively, expensive, dedicated hard-wired circuit boards have been implemented to perform Doppler processing fast enough for real-time display.

SUMMARY OF THE INVENTION

According to the invention, a method for generating color Doppler images is implemented in real time using digital processing steps implemented on multi-purpose microprocessors. An advantage of such method is that the method is implementable on commercial processors. This distinguishes over prior methods in which hard wired circuits dedicated to the Doppler calculation were required to achieve the necessary speed or where functionality or accuracy were sacrificed to achieve the necessary speed.

According to one aspect of the invention, the velocity estimated is not derived for every data sample. Instead, the velocity is estimated only when a tissue threshold decision for a given sample indicates that the sample is not tissue. This aspect of the invention frees up a substantial amount of processing time.

According to another aspect of the invention, arc tangent calculations are performed using simplified look-up tables without sacrificing accuracy. The simplified look-up tables allow arc tangent to be obtained using substantially less memory than in conventional look-up tables.

According to another aspect of the invention, the color Doppler processing is optimized using parallel, pipeline processing. In addition, direct memory access techniques are provided which perform input and output transfers in parallel with the processing functions, so that the transfer times do not slow down image processing and display steps. The result is a method for color Doppler processing which runs in real-time on various, commercially available multiprocessors.

According to an embodiment of this invention, ultrasound image data is derived by defining an active region of an image plane where flow velocity is of interest and receiving gray-scale tissue values for each pixel of the image plane. For each one pixel of the image plane outside the active region, the gray-scale tissue value is used to define the corresponding one pixel. Each gray-scale tissue value is tested for each pixel in the active region to determine whether the gray-scale value is in excess of a given threshold. For each tested gray-scale tissue value which does exceed the threshold, the tested gray-scale tissue value is used to derive a corresponding output pixel. For each tested gray-scale tissue value which does not exceed the threshold, a flow velocity value is derived and used to derive the corresponding output pixel. Flow velocity values are not derived for each tested gray-scale tissue value which does exceed the threshold and for each pixel of the image plane outside the active region.

According to an ultrasound system embodiment of this invention, an integrated circuit having a processing unit, a programmable direct memory access controller, a first memory module, and a second memory module on a common substrate are used to process velocity data. A sequence of frames of ultrasound data derived from scanning a target area in which an n-th ultrasound data frame is followed by an n+1-th, then an n+2-th ultrasound data frame. The system also includes a display unit for displaying an image frame derived from one or more of the sequence of frames of ultrasound data. The processing unit is programmed to derive flow velocity values for any given frame of the sequence of frames. The direct memory access controller is programmed to input the ultrasound data for alternating frames in alternating memory modules of the first and second memory modules. The direct memory access controller inputs ultrasound data for the n-th frame into the first memory module. While the processing unit derives flow velocity values for the n-th frame of ultrasound data stored in the first memory module, the direct memory access controller inputs ultrasound data for the n+1-th frame into the second memory module. While the processing unit derives flow velocity values for the n+1-th frame of ultrasound data stored in the second memory module, the direct memory access controller outputs flow velocity values derived previously for the n-th frame from the first memory module, and inputs ultrasound data for the n+2-th frame of ultrasound data into the first memory module. Te flow velocity values output from the first memory module are used to derive pixel data for an image frame output to the display. Th sequence of frames of ultrasound data is processed and a corresponding sequence of image frames are derived and output to the display for real-time viewing of a scanned target area.

According to another aspect of this invention, a flow velocity value is derived for a sample point within a target area scanned by a plurality of ultrasound signals, the flow velocity value corresponding to an arc tangent of a first lag of an autocorrelation of a series of in-phase and quadrature values of ultrasound signals. The series of ultrasound signals is collected over time at the sample point. The arc tangent is determined in which a numerator value is an imaginary component of the first lag of the autocorrelation series and a denominator value is a real component of the first lag of the autocorrelation series. The phase of the flow velocity value resides in one of a first quadrant, a second quadrant, a third quadrant, or a fourth quadrant. The method includes multiple steps. Where the absolute value of the numerator value is less than the absolute value of the denominator value, a first index is derived from the ratio of the absolute value of the numerator value to the absolute value of the denominator value. The first index is used to access a first look-up table having $2^x$ values. The first look-up table is linearly quantized in a fixed step increment of $\frac{1}{2^x}$ to achieve a first value, wherein x is a prescribed bit precision for the look-up table values. When the absolute value of the numerator value is greater than the absolute value of the denominator value, a second index is derived instead from the ratio of the absolute value of the denominator value component to the absolute value of the numerator value. The second index is used to access a second look-up table having $2^x$ values, which is nonlinearly quantized in a variable increment of $2^x/\{(2^x-u)(2^x-(u+1))\}$ to achieve the first value, where u is the u-th step increment and is not greater than $2^x$. For a non-negative numerator value and a non-negative denominator value, the first value corresponds to the flow velocity at the sample point and the phase of the flow velocity value occurs in the first quadrant. For a negative numerator value and a non-negative denominator value, the first value is transposed into the second quadrant, the transposed value corresponding to the flow velocity at the sample point and the phase of the flow velocity value occurs in the second quadrant. For a negative numerator value and a negative denominator value, the first value is transposed to the third quadrant, the transposed value corresponding to the flow velocity at the sample point and the phase of the flow velocity value occurs in the third quadrant. For a non-negative numerator value and a negative denominator value the first value is transposed to the fourth quadrant, the transposed value corresponding to the flow velocity at the sample point and the phase of the flow velocity value occurs in the fourth quadrant.

These and other aspects and advantages of the invention will be better understood by reference to the following detailed description taken in conjunction with the accompanying drawings.

BRIEF DESCRIPTION OF THE DRAWINGS

FIG. 13 is a chart of the pipelined execution of the color Doppler processing method for a processor capable of performing 1 multiply operation, 1 add/subtract operation, 1 load/store operation and 1 branch operation during 1 cycle, wherein operations for processing one pixel are shown;

FIG. 14 is a chart of the pipelined execution of the color Doppler processing method for a processor capable of performing 1 multiply operation, 1 add/subtract operation, 2 load/store operations and 1 branch operation during 1 cycle, wherein operations for processing one pixel are shown;

FIG. 15 is a chart of the pipelined execution of the color Doppler processing method for a processor capable of performing 1 multiply operation, 2 add/subtract operations, 2 load/store operations, and 1 branch operation during 1 cycle, wherein operations for processing one pixel are shown; and FIG. 16 is a table of the number of cycles executed to process one pixel of color Doppler image data under various scenarios using just one DSP of the multiprocessor of FIG. 4, wherein the worst case scenario is 22 cycles.

DESCRIPTION OF SPECIFIC EMBODIMENTS

Exemplary Host Platform

Figure 1:
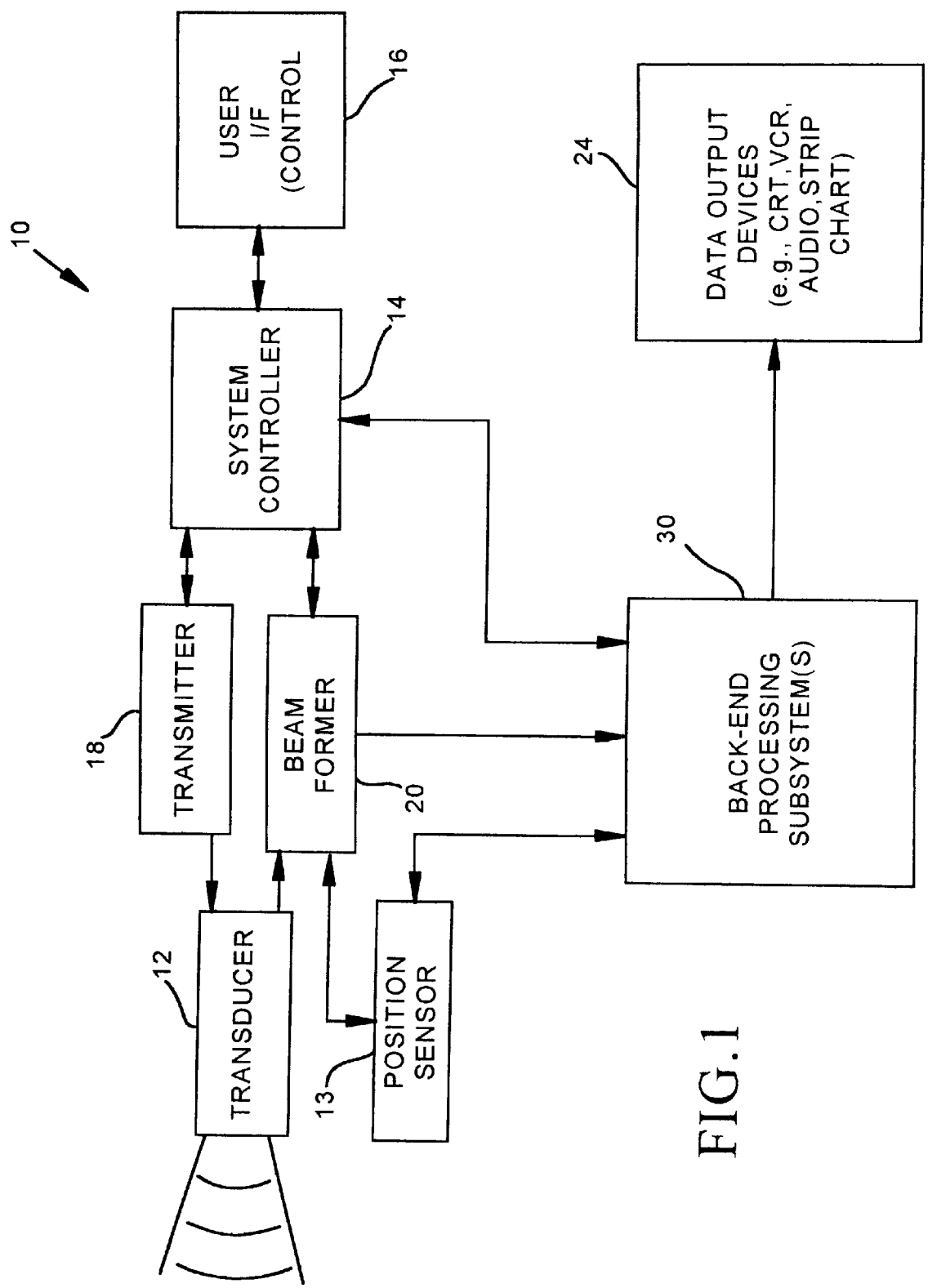
FIG. 1 is a block diagram of an ultrasound medical diagnostic imaging system.

FIG. 1 shows a block diagram of a host ultrasound medical diagnostic imaging system 10 for implementing a method embodiment of this invention. The function of the system 10 is to perform diagnostic imaging of a patient using ultrasound data. Ultrasound signals are transmitted via a transducer 12 into a patient. Reflected signals are detected and used to derive internal images of the patient for a scanned area/volume.

A system controller 14 receives and displays user control information via a user interface 16. During operation, system control signals are output to an ultrasound front end (i.e., transducer 12, a transmitter 18, a beam-former 20, and related circuitry) and to various subsystems. Transmitter 18 generates output signals to transducer 12 to define aperture, apodization, focus, and steering of ultrasound signals. Transducer 12 is an array of transducer elements. The elements define multiple channels, each channel for transmitting and/or receiving ultrasound signals. Transmitted ultrasound signals are in part absorbed, dispersed, refracted, and reflected when travelling through a patient. Reflected signals are sensed by transducer 12 and captured as a patterned beam by beam-former 20. The captured signals are sent to one or more back-end processing subsystems 30. The function of the back-end processing subsystem(s) 30 is to process the raw beam data and generate image data for output devices 24.

Figure 2:
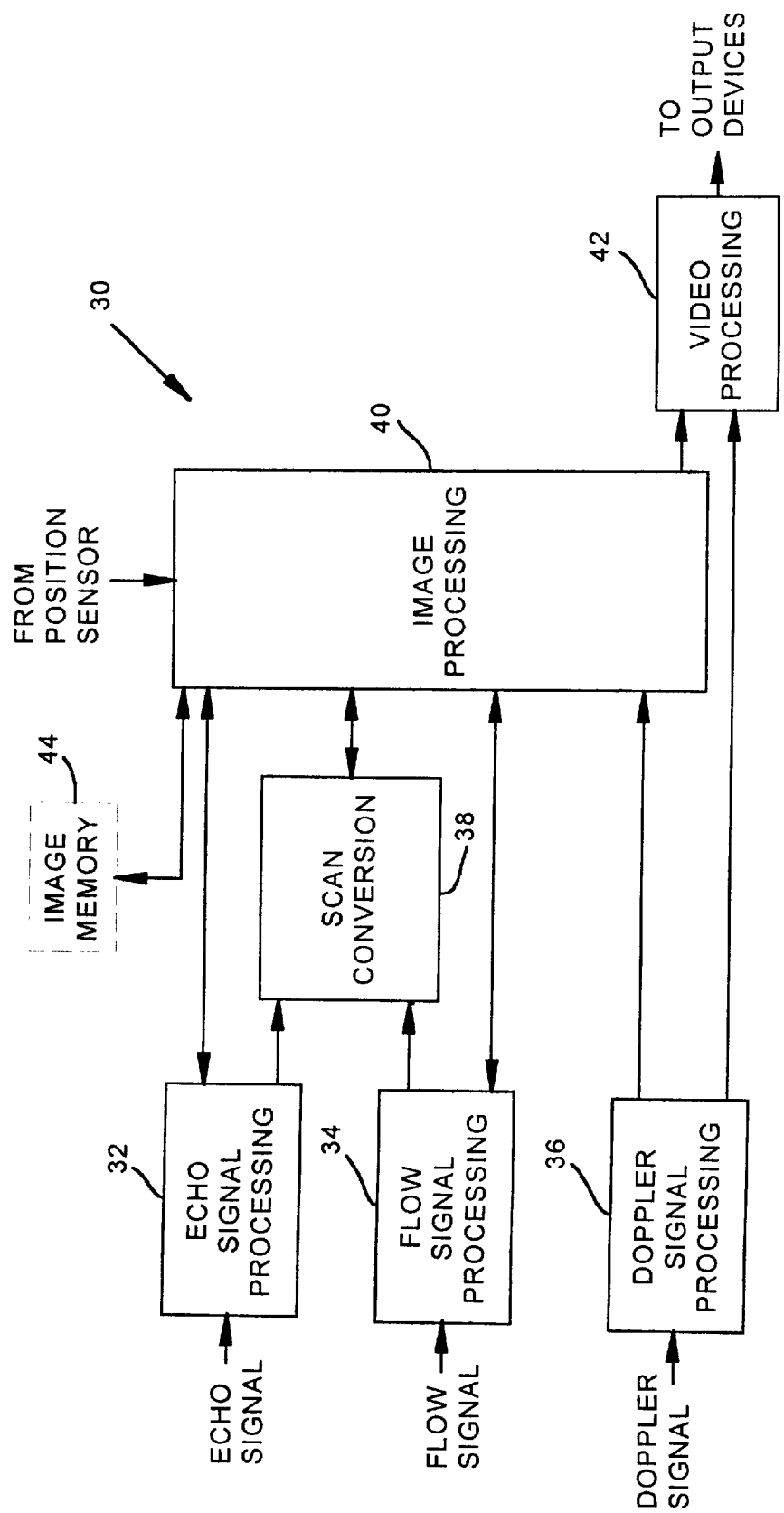
FIG. 2 is a control flow diagram of back-end processing tasks.

FIG. 2 is a block diagram of back-end processing tasks 32–42. Input signals are received at the back-end processing subsystem(s) 30 according to various modes of operation. In one embodiment there are one or more processor boards respectively programmed to perform one or more of the tasks 32–42. In a preferred embodiment the back-end processing subsystem(s) 30 are implemented with at least one programmable processor board to perform one or more tasks 32–42, and 0 or more dedicated boards to perform, respectively, 0 or more of the remaining tasks 32–42.

The input signals received at the back-end subsystem(s) 30 are referred to herein as vector signals. For a transducer 12 performing sector scanning, the vector signals are digital polar-coordinate data samples of echo, flow, and/or Doppler signals. For a transducer 12 performing linear scanning, the vector signals are digital cartesian-coordinate data samples of echo, flow, and/or Doppler signals.

The back-end processing tasks include echo signal processing 32, flow signal processing 34, Doppler signal processing 36, scan conversion 38, image processing 40, and video processing 42. Echo signal processing 32 typically encompasses signal enhancement filtering, energy detection, and image enhancement filtering. Various filtering and convolution techniques are employed. The purpose of echo signal processing 32 is to enhance the signal-to-noise ratio of the echo signal. Flow signal processing 34 analyzes signals for flow parameters. Typical parameter derivations include sample correlation and flow averaging. The purpose of flow signal processing 34 is to identify flow and turbulence within a scanned area. Doppler signal processing 36 typically encompasses signal enhancement filtering, spectral estimation processing, energy detection, and derived waveform filtering. The purpose of Doppler signal processing 36 is to identify and filter out Doppler shift, to improve spectral frequency response and to coordinate spectral mapping.

A scan conversion process 38 converts the processed vector data streams from echo signal processing 32 and flow signal processing 34. For polar-coordinate vector data, the data is converted into cartesian-coordinate raster data. For cartesian-coordinate vector data, the data is scaled into cartesian-coordinate raster data.

Image processing 40 includes image enhancement and processing executed on the raster data or vector data. In an off-line delayed playback (e.g., cine playback) mode of operation image data, vector data and/or raster data is received from image memory 44 and processed. Image processing 40 includes the volume or planar reconstruction and image visualization methods.

Video processing 42 executes on the image processed data to generate video signals, audio signals, and graphing signals for output to a display device, audio device, storage device (e.g., VCR), and/or charting device. Video processing 42 in some applications also executes on Doppler processed vector data to generate similar video signals, audio signals, and graphing signals for output to the display device, audio device, storage device, and/or charting device.

Figure 3:
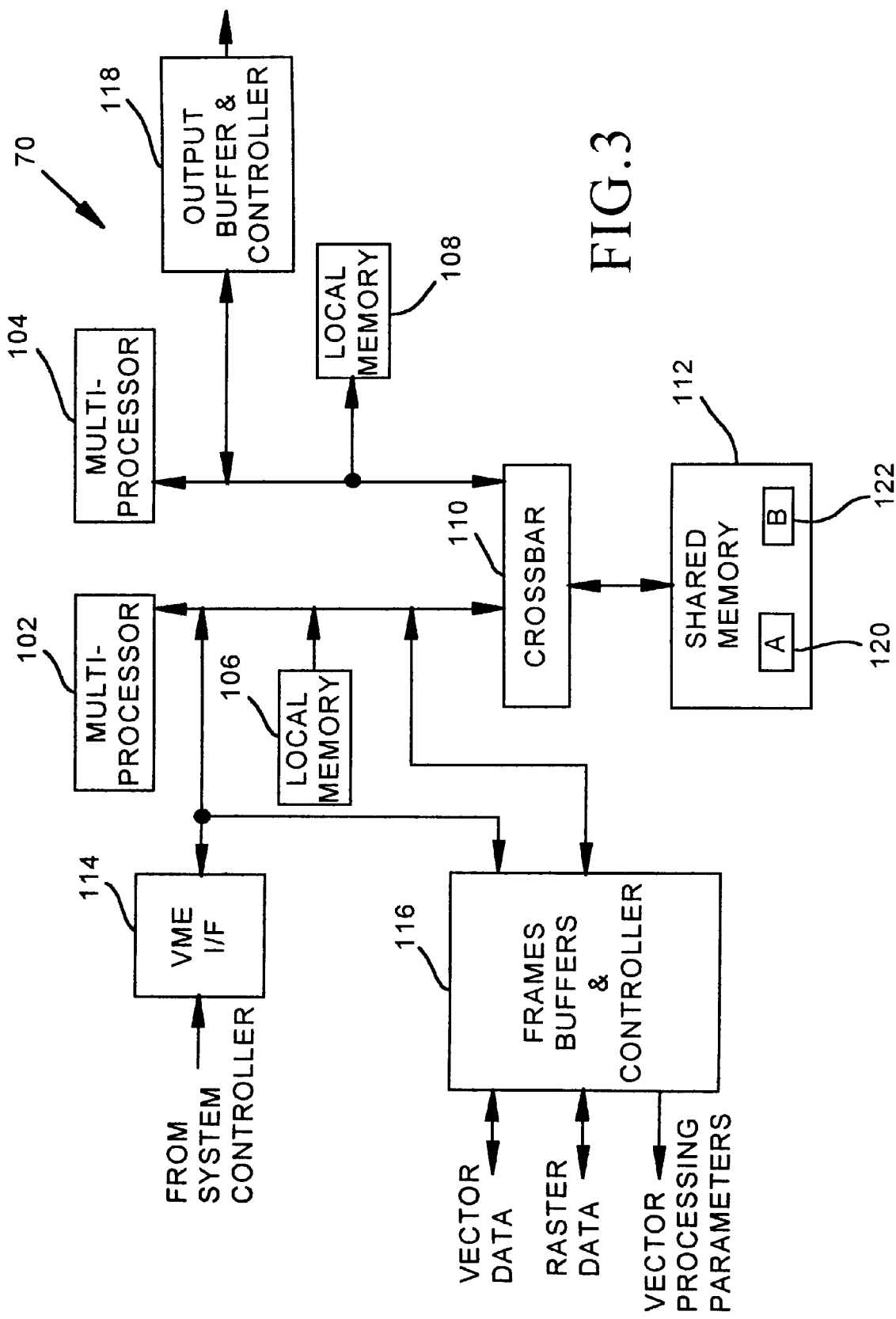
FIG. 3 is a block diagram of the programmable ultrasound signal processing apparatus for implementing the method of this invention.

FIG. 3 is a block diagram of a programmable processor subsystem 70 for implementing one or more of the tasks 32–40. In a preferred embodiment subsystem 70 embodies or is part of the back-end subsystem(s) 30. In another embodiment subsystem 70 is an external processing subsystem receiving data from a subsystem 30 or other part of the system 10. Apparatus 70 includes multiple processors for performing various vector processing, image processing, scan conversion and/or video processing tasks. In a specific embodiment a pair of processors 102, 104 are included. The apparatus 70 also includes local memory 106, 108, crossbar switch 110, shared memory 112, interface 114, frame buffer/controller 116 and output buffer/controller 118.

Figure 4:
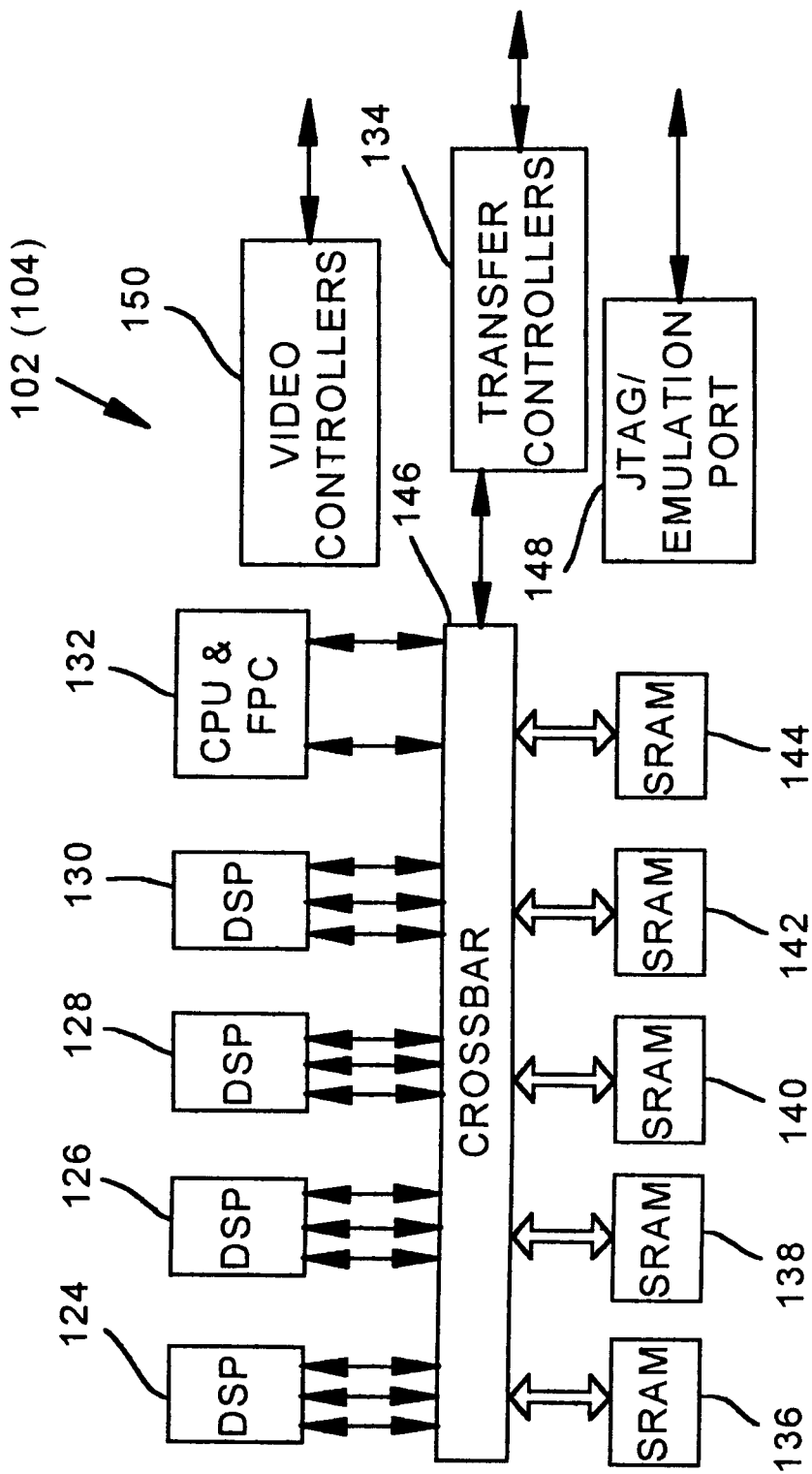
FIG. 4 is a block diagram for one embodiment of a multiprocessor of FIG. 3.

In one embodiment each processor 102, 104 includes one or more digital signal processors. In a specific embodiment each processor 102, 104 is a multiprocessor, such as a Texas Instruments multimedia video processor ("MVP") (part no. TMS320C80). FIG. 4 shows a block diagram of an MVP multiprocessor. The MVP combines on a single semiconductor chip, four fully programmable digital signal processors 124, 126, 128, 130 and a master processor 132 for handling multiple data streams via a transfer controller 134. Several on-chip random access memory (RAM) devices 136, 138, 140, 142, 144 serve as resident memory accessible to the digital signal processors (DSPs) 124–130 via a crossbar network 146. The MVP has a throughput rating of approximately 2 billion operations per second. The master processor 132 is a RISC processor with an integral floating point unit. According to this embodiment the master processor 132 coordinates and distributes processing tasks among the DSPs 124–130 and manages external off-chip communications. A JTAG/emulation port 148 is included for aid in testing, development and diagnostics.

Each DSP 124–130 includes two address generators, three input 32-bit ALUs, a 16×16 multiplier, three zero-overhead loop controllers, and a 32-bit barrel shifter. Each RAM 136–144 has a 10 kB capacity providing 50 kB of single-cycle SRAM. Memory 136–144 is partitioned in blocks with each block serving as either data RAM, parameter RAM, data cache or instruction cache. The transfer controller 134 services the on-chip caches and interfaces to external memory (e.g., local memory 106 or 108, and shared memory 112).

The MVP also includes a pair of video controllers 150. Controllers 150 generate video synchronization signals or synchronize data transfer rates with external video signals.

Referring again to FIG. 3, each multiprocessor 102, 104 has a respective dedicated local memory 106, 108, serving as a secondary cache. Each local memory 106, 108 has capacity for storing a frame of ultrasound data. In one embodiment a 2 MB capacity is provided at each local memory 106, 108. In addition shared memory 112 is included. In one embodiment shared memory 112 is implemented as two separate 64 MB memory banks 120, 122 for a total of 128 MB shared memory. The storage capacity of local memory 106, 108 and shared memory 112 varies for alternative embodiments. The multiprocessors 102, 104 access shared memory through crossbar switch 110. For a two multiprocessor embodiment, a 2×2 crossbar switch is implemented. The purpose of the crossbar switch 110 is to allow the multiple processors 102, 104 simultaneous access to the shared memory banks. The crossbar switch 110 includes a pair of transceivers for each input channel, along with a crossbar controller.

The function of the crossbar controller is (i) to manage requests for access and (ii) to refresh shared memory 112. If a multiprocessor 102 requests access to a shared memory bank 120, 122 not currently being accessed by the other multiprocessor 104, then the access is granted. If the multiprocessor 102 requests access to a shared memory bank 120, 122 currently being accessed, then the multiprocessor 102 waits until the memory bank is available. Simultaneous access to a shared memory bank 120, 122 thus is available when the accesses are to separate memory banks. For reconciling simultaneous requests for access, one multiprocessor 102 is prescribed to have priority for a specific one shared memory bank 120, while the other multiprocessor 104 is prescribed priority for the other shared memory bank 122. If both multiprocessors 102, 104 request access to a common bank, then the processor with the prescribed priority for that bank is granted access. However, to avoid lengthy delays, the other multiprocessor is granted access after the current access, even if the higher priority multiprocessor comes right back with a second request. For example, consider the case in which multiprocessor 102 has the prescribed priority to the first memory bank 120. The first multiprocessor 102 makes two sequential requests for access to bank 120, while multiprocessor 104 also makes a request to bank 120. Because of the prescribed priority, the first multiprocessor 102 is granted access for its first request. Next, however, the second multiprocessor 104 is granted access. Then, the first multiprocessor 102 is granted access for its second request.

System control signals are received by apparatus 70 from the system controller 14 via an interface 114. The frame buffer/controller 116 serves as a data interface with the ultrasound front end (e.g., beamformer 20), the back-end processing subsystem 30, or another subsystem 30. The output buffer/controller 118 serves as a data interface between the apparatus 70 and the back-end processing subsystem 30 or another subsystem 30, and/or one or more output devices.

Processing Overview

Figure 5:
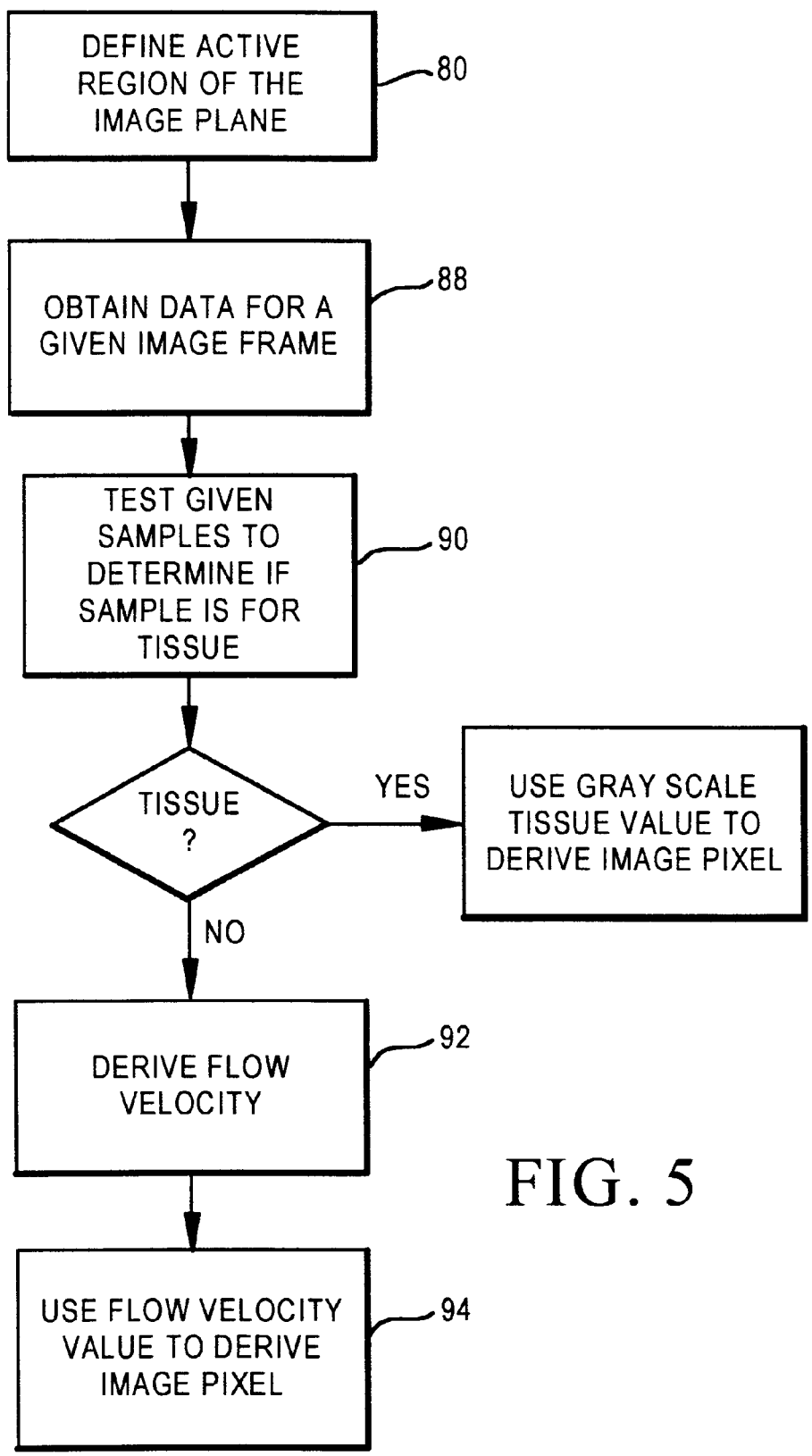
FIG. 5 is a flow chart of the tissue versus flow decision processing according to an embodiment of this invention.
Figure 6:
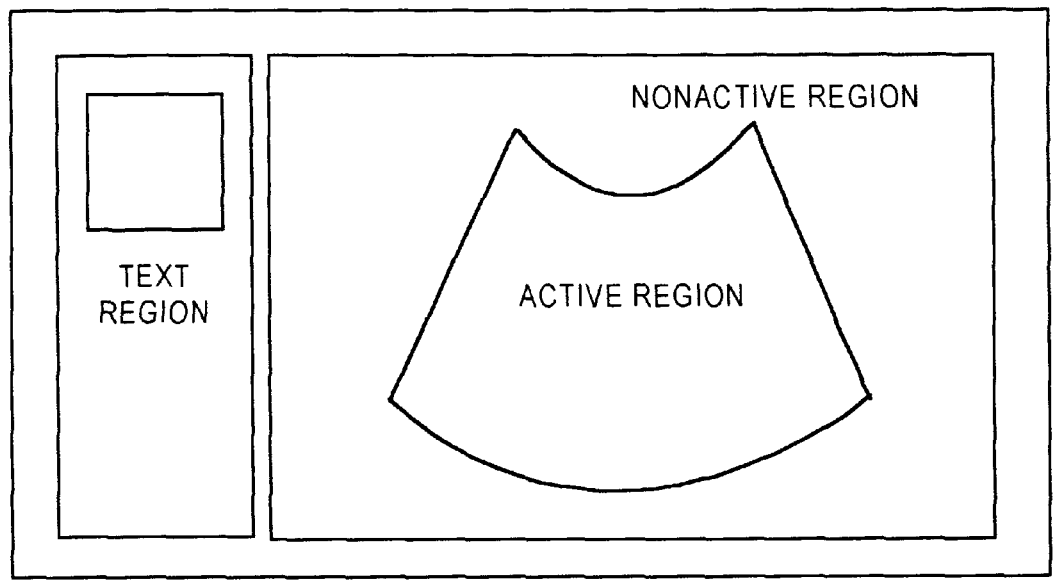
FIG. 6 is a diagram of a display image are having an active area and a non-active area.

FIG. 5 shows an overview of processing according to a method embodiment of this invention. At one step 80 an active region 84 of an image plane is defined within which flow velocity is of interest. FIG. 6 shows a display area 82 having an active region 84 and a non-active region 86. At step 88 ultrasound data for a given frame is collected by the transducer 12 and passed through the beamformer 20 and into a back end processing subsystem 30 for processing. A gray scale tissue value is computed for each data sample within an echo signal processing subsystem 32. At step 90 each gray-scale tissue value for each pixel of the active region 84 is tested to determine whether the value exceeds a tissue threshold value. If the gray-scale tissue value for a given pixel does exceed the threshold value, then the gray-scale tissue value is used to generate a display image pixel. At step 92, if the gray-scale tissue value does not exceed the threshold, then a flow velocity value is derived. At step 94, the flow velocity value is used to generate a display image pixel. Of significance is that the flow velocity is not derived for a given pixel when the gray-scale tissue value test determines that the value corresponds to tissue.

Color Doppler Processing

Figure 7:
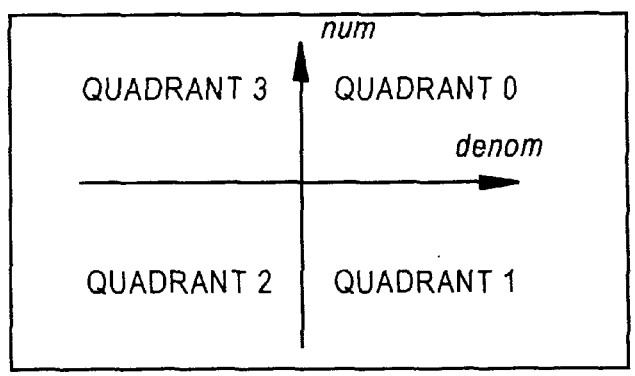
FIG. 7 is a diagram of quadrants for a num-denom coordinate plane.

Doppler data samples are received over both a time range and a spatial range. The number of samples taken per spatial location over time typically is small (e.g., not more than 16). A set of data samples from a specific spatial location over time is called an ensemble. An autocorrelation function is used to determine the Doppler frequency for a given ensemble. The Doppler frequency is taken to be the mean frequency of the ensemble. As described in the background section, the mean frequency is proportional to the phase of the mean output sample of the first lag of the autocorrelation function, as given below:

$$\overline{\Delta\Phi} = \text{full arctan} \frac{\sum_{h=0}^{E-1} Q_h I_{h-1} - Q_{h-1} I_h}{\sum_{h=0}^{E-1} I_h I_{h-1} + Q_h Q_{h-1}} = \text{full arctan} \frac{\text{num}}{\text{denom}}$$

where E is the number of the complex-number samples per ensemble. The numerator is herein referred to as 'num,' while the denominator is referred to as 'denom.' FIG. 7 shows quadrants for the arc tangent angles in a plot of num versus denom. Num is represented along the vertical axis. Denom is represented along the horizontal axis. There are four quadrants 0–3.

According to a preferred embodiment num and denom each are represented by n bits. The arc tangent of this ratio is determined from a look-up table. The ratio num/denom is used as an index into such look-up table. Because a division is a slow computation, in one embodiment the ratio is calculated by multiplying num with the reciprocal of the denom. The reciprocal of denom is read from a reciprocal look-up table having $2^n$ entries. The look-up table is stored in RAM (e.g., SRAM 136, 138, 140, 142 or 144).

If both the absolute value of num (i.e., abs(num)) and the absolute value of denom (i.e., abs(denom)) are n bits, then the ratio of num to denom can be any real number ranging from 0 to $2^n-1$. A total of n+x bits is therefore needed for the index. A quantization step of $\frac{1}{2}^x$ is used to achieve desired accuracy. If, for example, n=12 bits and it is desired to have numbers accurate to 0.0005, then x=11. Thus 23-bit indices would be required for such arc tangent look-up table embodiment. If the arc tangent look-up table entries are 8 bits, then 8 Mbytes of high speed memory is needed for the look-up table. According to an aspect of the invention, however, accurate results are achievable using a smaller amount of high speed memory.

Figure 8:
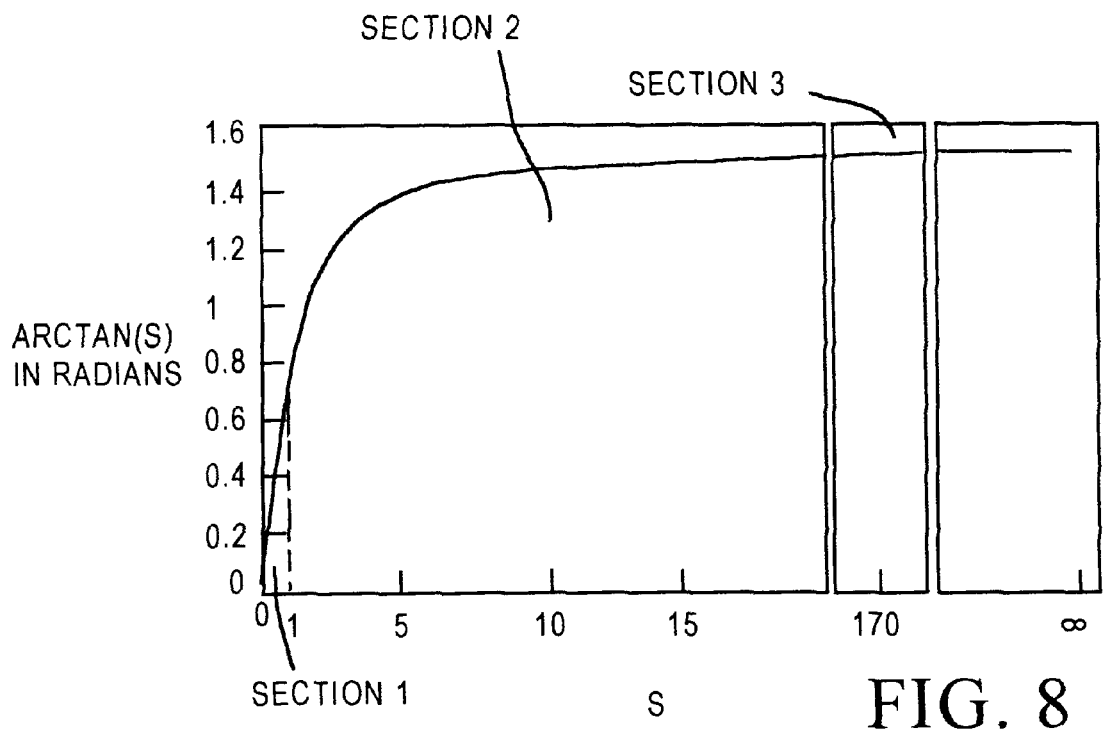
FIG. 8 is a graph of an arc tangent function.

FIG. 8 is a graph of the arc tangent function in radians, where s is the ratio of abs(num) to abs(denom). When s is from 0 to about 1, the arc tangent function is linear with an approximate slope of π/4. When s is from 1 to about 64, the arc tangent function is nonlinear. When s is from 64 to infinity, the arctangent is linear with a slope of approximately 0. The varying slopes make it difficult to select a linear quantization step size for entries in a look-up table which would be accurate for the entire range of the ratio, s. According to aspects of this invention, the size of the arc tangent look-up table is reduced and its accuracy is achieved by having two smaller arc tangent look-up tables. One look-up table is quantized linearly. The other look-up table is quantized nonlinearly.

Referring again to FIG. 8, the region where s goes from 0 to 1 is a first section of the arc tangent function. The region where s goes from 1 to 64 is a second section. The region where s is greater than 64 is a third section. Arc tangent values for section 1 are obtained from the first look-up table. Arc tangent values for sections 2 and 3 are obtained from the second look-up table. Each of the first and second arc tangent look-up tables are loaded into RAM (e.g., SRAM 136, 138, 140, 142 and 144) before color Doppler processing is performed. In an alternative embodiment the two look-up tables are implemented in memory as one table having two different methods for indexing into the table. One method indexes into the combined table as if accessing the first (linear-quantized) look-up table. The other method indexes into the combined table as if accessing the second (nonlinearly-quantized) look-up table.

With num and denom calculated for a given ensemble, the num is tested relative to the denom. If num is less than or equal to denom, then the resulting fraction is an x-bit ratio, r. The ratio, r, is used as an index into the linearly-quantized first arc tangent look-up table. The values in the first arc tangent look-up table apply to quadrant $0$ (i.e., 0 to $\pi/4$), since the ratio, r, is always less than or equal to one. The entries in the first arc tangent look-up table are linearly quantized with a quantization step (i.e., difference between successive index values) of $\frac{1}{2}^x$. There are $2^x$ entries in the linearly-quantized first arc tangent look-up table.

Figure 9:
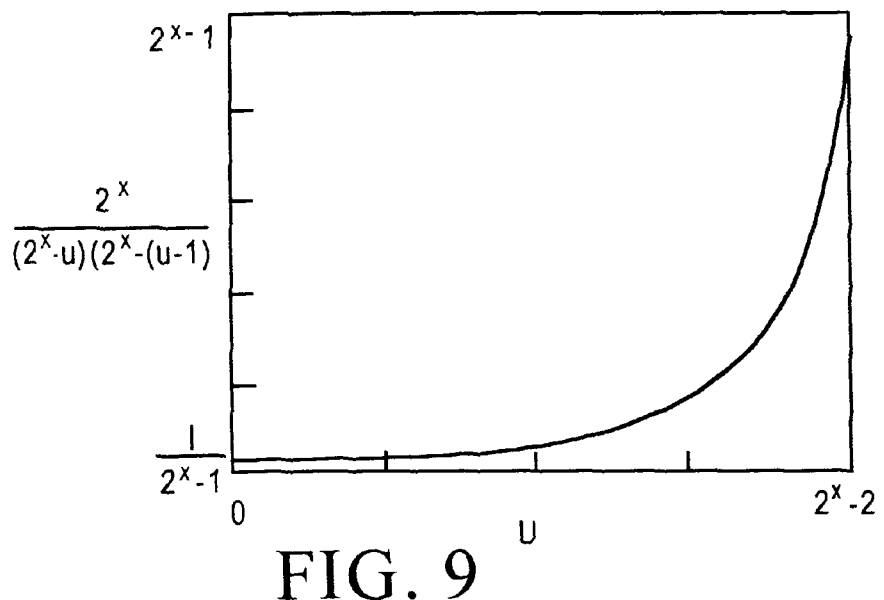
FIG. 9 is a graph of a difference between successive rations of num/denom for a nonlinearized section of the arc tangent function of FIG. 6.

When num is greater than denom, the num and denom values are swapped. The resulting fractional x-bit ratio, t (i.e., t=abs(denom) to abs(num)) is used as an index, t, into the non-linearly-quantized second arc tangent look-up table. The values in second arc tangent look-up table apply to quadrant $1$ (i.e., $\pi/4$ to $\pi/2$). There are $2^x$ entries in the second arc tangent look-up table. Because t represents an inverted argument, the $2^x$ locations represent the abscissa of the arc tangent function of FIG. 8 as follows:

$$\frac{2^x}{2^x - u}, 0 < u \leq 2^x - 1$$

where u is the u-th address of second arc tangent look-up table. The quantization step between successive ratio t values for the second arc tangent look-up table is given by:

$$\frac{2^x}{2^x - (u+1)} - \frac{2^x}{2^x - u} = \frac{2^x}{(2^x - u)(2^x - (u+1))}$$

which is plotted in FIG. 9. Larger quantization steps occur as u increases. Compared to a linear quantization, this nonlinear quantization allows many more entries to be allocated to the beginning portion of section 2 of the arc tangent function (see FIG. 8). The ever increasing quantization step size used for section 2 and 3 of the arc tangent function provides as much accuracy as the linear quantization for section 1.

It has been found that the entries corresponding to the second arc tangent look-up table are equal to $\pi/2$ minus a corresponding entry in the first look-up table. This can be shown as follows:

$$\tan\left(\frac{\pi}{2} - 1\right) = \frac{\sin\left(\frac{\pi}{2} - 1\right)}{\cos\left(\frac{\pi}{2} - 1\right)} = \frac{\cos(1)}{\sin(1)} = \frac{1}{\tan(1)}$$

$$\arctan\left(\frac{1}{1}\right) = \frac{\pi}{2} - \arctan(1)$$

Thus, in one embodiment the second arc tangent look-up table is not embedded in memory. Instead one indexes into the first arc tangent look-up table and performs the above substraction operation.

Figure 10:
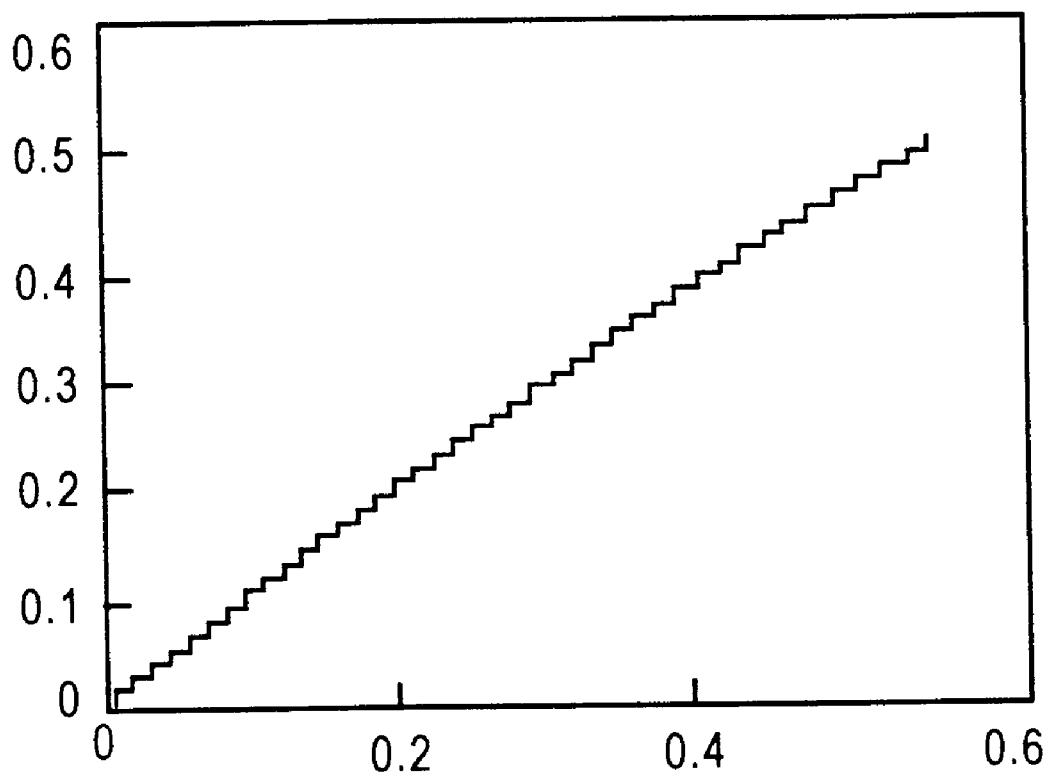
FIG. 10 is a graph of a linearly-quantized section of an arc tangent function.

FIG. 10 shows the beginning of the arc tangent function represented by 4096 entries among two arc tangent look-up tables. The first 2048 samples are linearly quantized and correspond to section 1 of the arc tangent function. These entries are in the first arc tangent look-up table. The quantization step in this region is 1/2048. Although the input quantization step size is 1/2048, the horizontal steps as shown in FIG. 10 are larger than 1/2048. This is because the arc tangent function values are represented in 8 bits and there are only 256 quantized output levels. When the input changes by 1/2048, the output value in many instances does not change enough to push the quantized output to a next higher value.

The second 2048 samples are nonlinearly quantized and cover the range from s=1 to s=infinity (i.e., sections 2 and 3 of the arc tangent function of FIG. 8). These entries are in the second arc tangent look-up table. The varying input quantization step is $2048/((2048-u)(2047-u))$, where u goes from 1 to 2047.

In one embodiment blood flow velocity computations are further simplified by embedding the scaling factor of $1/\pi$ into the first and second look-up tables so that each entry represents $\theta/\pi$. To speed up the magnitude calculation, the input thresholds are squared. In this way no square root operations are required. Instead, the sum of squared values $num^2$ plus $denom^2$ is computed. When num and denom are 12 bits, the sum of squared values requires 24-bit precision and takes 60 ms for a total execution time of 190 ms for computing the velocity and magnitude values on a TMS 320C80 processing unit. This is faster than the 256 ms achieved with the conventional coordinate rotation digital computer (CORDIC) algorithms.

Figure 11:
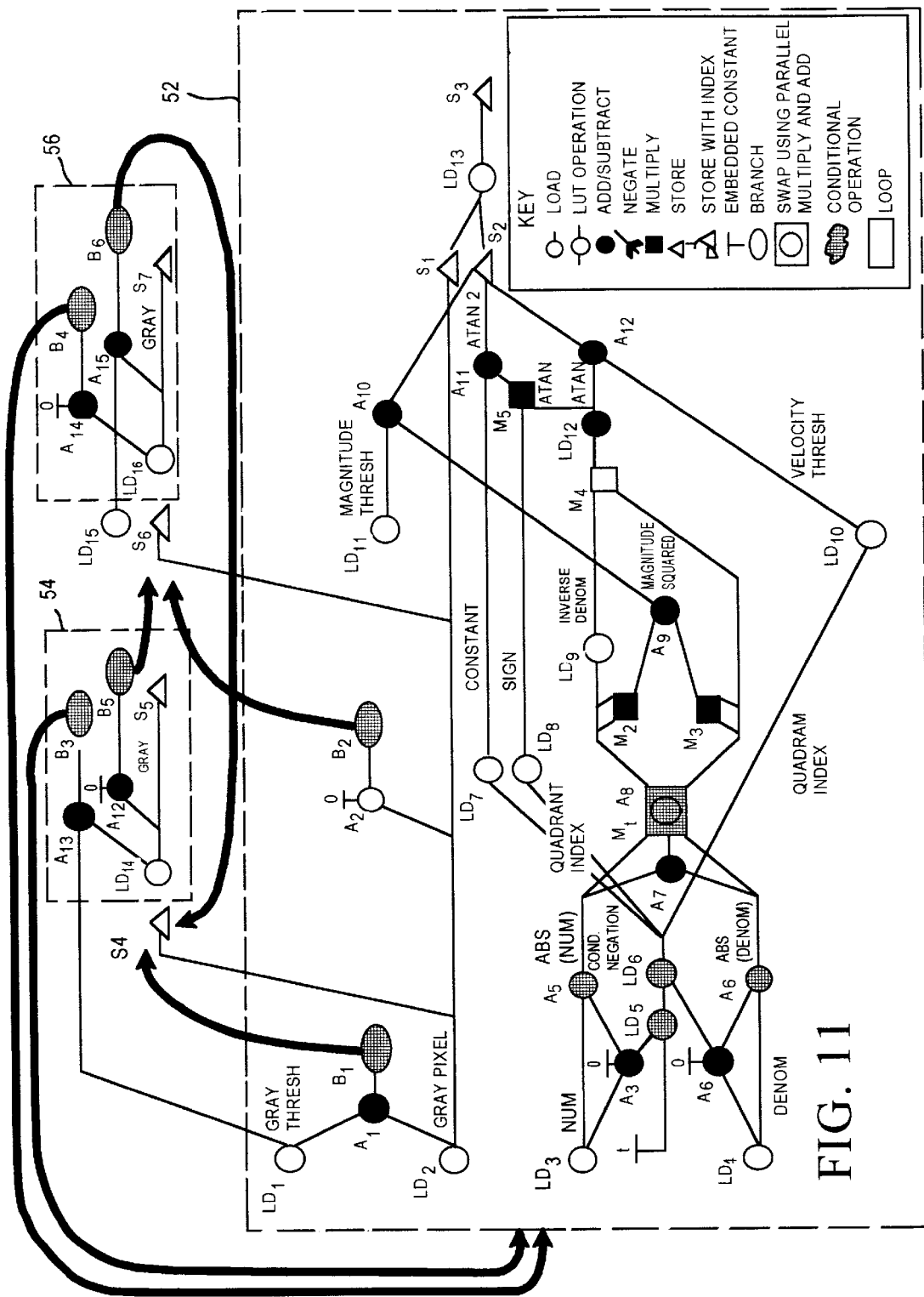
FIG. 11 is a processing flow graph for color Doppler image generation according to an embodiment of this invention.
Figure 12A:
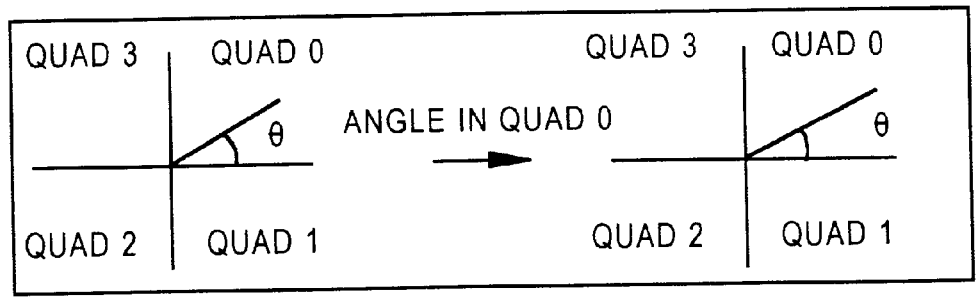
FIGS. 12a–d are charts depicting the conversion of arc tangent angle into a full arc tangent angle.
Figure 12B:
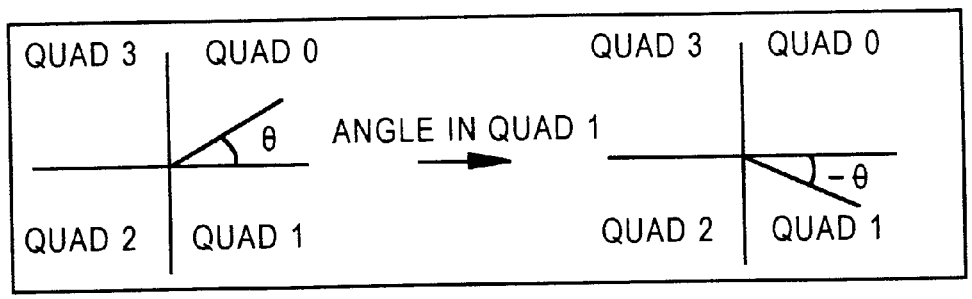
Figure 12C:
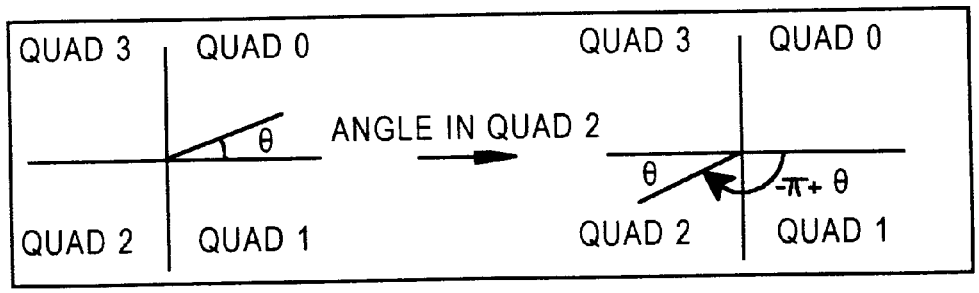
Figure 12D:
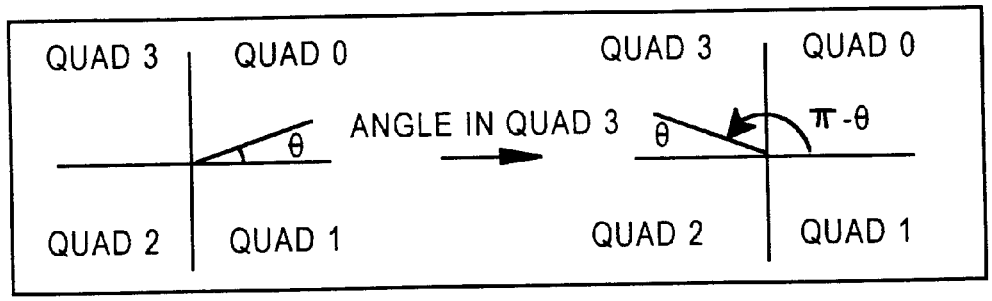

FIG. 11 shows a flow graph 50 of the Doppler processing method. The method begins in a loop 52 where the velocity computations and tissue flow decision tasks are performed. At operations $LD_1$ and $LD_2$ gray scale threshold and gray-scale pixel values are loaded, respectively. The gray-scale pixel is compared to the gray-scale threshold at operation $A_1$ and to zero at operation $A_2$. If the gray-scale pixel value is larger that the threshold value, then processing branches at operation $B_1$ to a separate gray-scale pixel processing loop 54. Processing loop 54 does not include velocity computations. Thus it generates an output display pixel value faster. The operations in loop 54 include a load operation $LD_{14}$, a store operation $S_4$, addition/substraction operations $A_{13}$ and $A_{12}$, and conditional branch decisions, $B_3$ and $B_5$. If the gray scale pixel value is zero, then at operation $B_2$, processing branches to loop 56. Processing loop 56 also do not include velocity computations. The operations in loop 56 include load operations $LD_{15}$ and $LD_{16}$, a store operation $S_6$, addition/substraction operations $A_{14}$ and $A_{15}$, and conditional branch decisions, $B_4$ and $B_6$. The end result of either loop 54 or 56 is a tissue value stored for display at operation $S_5$ or $S_7$, respectively.

If a gray scale pixel is not bright enough to exceed the tissue threshold value, and is not zero-valued, then processing continues within loop 52. Load operations $LD_3$ and $LD_4$ bring in the num and denom values. The quadrant is initially assumed to be $0$. If num is found to be negative at operation $A_3$, it is made positive at operation $A_5$, and the quadrant value is changed to quadrant 1. If denom is found to be negative at operation $A_4$, then it is made positive at operation $A_6$, and the quadrant value is set to quadrant 2 or 3 depending on whether num was positive or negative at step $LD_6$. At operation $A_7$ num and denom are compared to see if num is greater than denom. If num is greater, then num and denom are swapped in a single processing cycle. This is achieved by performing a multiplication and an addition in parallel, shown as operations $M_1A_8$. As previously described, the reciprocal of the denominator is determined by using the denominator as an index into a reciprocal look-up table during load operation $LD_9$. The ratio then is computed as the multiplication of num and the reciprocal at operation $M_4$. The ratio (e.g., r or t) then is used to access one of the arc tangent look-up tables in load operation $LD_{12}$.

The look-up table is scaled by a factor $1/\pi$. Thus, the result of the look-up is arc tangent divided by $\pi$. This result is compared at operation $A_{12}$, with a velocity threshold value, which is loaded in at operation $LD_{10}$. This typically is time consuming because the velocity threshold can vary from 0 to 1 while the intermediate results of the processing are a quadrant number and a $\theta/\pi$ value ranging from 0 to ½. For the velocity thresholding $\theta/\pi$ is converted into the absolute value of its full arc tangent over $\pi$ value. FIGS. 12a–d show the conversion for respective quadrants 0–3, where $\theta$ and a quadrant number are used to derive the angle. In the processing steps the $\theta/\pi$ value read from the linearly-quantized first look-up table or the nonlinearly quantized second look-up table is compared with the velocity threshold without taking any intermediate steps. When $\theta$ is in quadrant 0 or 1, the absolute value gives the same $\theta$. When $\theta$ is in quadrant 2, the absolute value derived is $\pi-\theta$. There is no need in taking the absolute value if thresholding is done on $\theta/\pi$ before it is converted to the full arc tangent value.

If the velocity threshold is between 0 and ½ and $\theta$ is in quadrant 0 or 1, then the angle is valid if $\theta/\pi$ is greater than or equal to the velocity threshold. If $\theta$ is in quadrant 2 or 3, then the angle is always valid since $(\pi-\theta)/\pi$ is always greater than the velocity threshold. This is implemented by taking a given velocity threshold, velocity_thresh, and constructing a velocity threshold look-up table which is indexed by the quadrant value as shown in Table 1:

TABLE 1

| Quadrant | Velocity Threshold |
| --- | --- |
| 0 | velocity_thresh |
| 1 | velocity_thresh |
| 2 | 0 |
| 3 | 0 |

This look up operation occurs in the load operation $LD_{10}$. A similar process is used when the velocity threshold is between ½ and 1. The difference is that if $\theta$ is in quadrant 0 or 1, the angle is always invalid. If $\theta$ is in quadrant 2 or 3, it is valid if:

$$\frac{\pi - \theta}{\pi} \geq \text{velocity\_thresh},$$

$$\frac{\theta}{\pi} \leq 1 - \text{velocity\_thresh}$$

This is implemented by taking a given velocity threshold, velocity_thresh, and constructing a velocity threshold look-up table which is indexed by the quadrant value as shown in Table 2:

TABLE 2

| Quadrant | Velocity Threshold |
| --- | --- |
| 0 | 1 |
| 1 | 1 |
| 2 | 1 - velocity_thresh |
| 3 | 1 - velocity_thresh |

If $\theta/\pi$ is determined to be invalid, then a flag is set and saved. The sum of the squared values $num^2+denom^2$ is computed in operations $M_2$, $M_3$ and $A_9$. This is compared with the magnitude threshold loaded at operation $LD_{11}$. If the magnitude is not valid as determined at operation $A_{10}$, then a flag is set and saved.

The $\theta/\pi$ value read from the first or second arc tangent look-up table is converted to the full arc tangent/$\pi$ value by adding or subtracting from a quadrant dependent constant. A sign look-up table is indexed by the quadrant number and accessed at operation $LD_8$ to retrieve either 1 or −1, indicating whether an addition or a substraction is to be performed. This sign is attached to $\theta/\pi$ by multiplication operation $M_5$. The quadrant-dependent constant is loaded from another quadrant-indexed look-up table at operation $LD_7$. This constant is then added to the signed $\theta/\pi$ value in operation $A_{11}$ to arrive at the estimated blood flow velocity.

The quadrant conversion is summarized as follows: When num is non-negative and denom is non-negative, the value from the arc tangent look-up table corresponds to velcoity and the phase of the flow velocity value occurs in the quadrant 0. When num is negative and denom is non-negative the value from the arc tangent look-up table is transposed to quadrant 1 and the phase of the flow velocity value occurs in quadrant 1. When num is non-negative and denom is negative, the value from the arc tangent look-up table is transposed to quadrant 2 and the phase of the flow velocity value occurs in the quadrant 2. When num is non-negative and denom is negative, the value from the arc tangent look-up table is transposed to quadrant 3 and the phase of the flow velocity value occurs in quadrant 3.

To output a correct pixel value, a 4-entry memory area is used. The gray scale pixel is always stored in the first entry at operation $S_1$. The two saved flags are used as an index into the memory area in storing the velocity pixel at operation $S_2$. The velocity pixel value is stored in the first entry of the memory area when both the velocity and the magnitude values are valid. The correct output pixel value as held in the first memory area of the 4-entry area is loaded at operation $LD_{13}$ and stored at operation $S_3$ for output and display.

Optimizing Computations through Pipeline Processing

To generate a single valid velocity output pixel there are 5 multiplications operations, 12 addition/substraction operations, 16 load/store operations and 2 branch operation as shown in FIG. 13. On a purely sequential processor, these operations would require at least 35 clock cycles. Using a superscalar/VLIW processor which allows one multiply, one add/subtract, one load/store and on branch operation per cycle, the velocity output pixel can be obtained in a worst-case 16 cycles. In such embodiment the load/store unit is the limiting unit. Output pixels can be generated even faster when gray-scale values are determined to be valid or zero since no velocity computation is required.

Using an alternative processor which supports one multiplication, one addition/subtraction, one branch and two load/store operations per cycle allows the velocity output value to be computed in a worst case of 12 cycles as shown in FIG. 14. The addition/subtraction unit is the limiting unit in this embodiment. If another addition/subtraction unit is included, then the velocity output computation can be performed in a worst case scenario of 8 cycles as shown in FIG. 15. Worst case scenario is the number of cycles needed to output a velocity pixel where the prior pixel was also a velocity pixel.

The MVP processor 102/104 of FIG. 4 includes 5 processors 124–132. Each of the five processors 124–132 is capable of executing multiple operations per cycle. Each DSP 124–130 can execute one 16-bit multiplication, one 32-bit arithmetic and logical operation, a branch, and two load/store operations in the same cycle. With the CPU 132 executing 2 operations and each DSP 124–130 executing four parallel operations, a total of 18 concurrent operations are achievable every cycle. Implementing the velocity computation on a single DSP of the processor of FIG. 4 allows the velocity computation to be computed as a worst case in 21 cycles, as shown in FIG. 16. With 4 DSPs four pixels can be processed at a time, effectively shortening the average number of cycles to generate a velocity pixel. Since the color Doppler processing velocity value computed is independent for each pixel, no inter DSP communications are needed, which might slow down the throughput. Thus, on average the MVP 102/104 is able to generate a velocity output pixel every 5.25 clock cycles (i.e., 21/4=5.25). For a 304×498 pixel output image, the worst case performance of the MVP 102/104 running at 50 MHz was measured to be 16.6 ms. A detailed analysis showed that the computations took 15.9 ms, while the input/output operations took 12.1 ms. Thus, the I/O time is completely transparent to the computation time.

In one embodiment there is a first and second arc tangent look-up table stored in RAM for use by each of two DSPs. Thus, there are two sets of the tables stored in the MVP 102/104 for use by the four DSPs 124–130. By mapping the address of the DSP memory module 1 adjacent to another DSPs memory module 0, a contiguous 4-kbyte reciprocal look-up table is implemented using only 2 kbytes of each DSPs SRAM. The first and second arc tangent look-up tables are constructed and shared in a similar manner.

The direct memory access controller for a given MVP processor 102/104 is the transfer controller 134 of FIG. 4. Such controller 134 is programmed to ultrasound data for alternating frames in alternating memory modules of multiple SRAM modules 136, 138 or 140, 142. The controller 134 inputs data into one memory module for an n-th frame of data. While the DSPs process the n-th frame, the controller 134 loads data for the n+1-th frame into the second memory module. While the DSPs derive flow velocity values for the n+1-th frame of ultrasound data stored in the second memory module, the direct memory access controller outputs flow velocity values derived previously for the n-th frame from the first memory module, and inputs ultrasound data for the n+2-th frame of ultrasound data into the first memory module. The values output from the first memory module are used to derive pixel data for an image frame output to the display. The sequence of frames of ultrasound data is processed and a corresponding sequence of image frames are derived and output to the display for real-time viewing of a scanned target area.

Meritorious and Advantageous Effects

For typical ultrasound systems, the maximum line-acquisition frequency is approximately 20 MHz. For an ensemble size, E, the time to acquire N lines of data is a minimum of (E*N)/20,000 seconds. The value of E is typically 16 or less, in 33 ms, for example, only 41.25 lines of data are acquired. Many more lines need to be acquired to generate 304×498 pixels for an image. Even with a vertical interpolation factor of 4, acquisition of 124 lines requires 99 ms. In such case, the Doppler processing method described above on an MVP processor 102/104 takes a maximum 17% of the processor time. The rest of the time may be allocated to other tasks.

Although a preferred embodiment of the invention has been illustrated and described, various alternatives, modifications and equivalents may be used. Therefore, the foregoing description should not be taken as limiting the scope of the inventions which are defined by the appended claims.

What is claimed is:

1. A method for deriving ultrasound image data, comprising the steps of:

defining an active region of an image plane where flow velocity is of interest;

receiving gray-scale tissue values for each pixel of the image plane;

for each one pixel of the image plane outside the active region, using the gray-scale tissue value to define said corresponding one pixel;

testing each gray-scale tissue value for each pixel in the active region to determine whether the gray-scale value is in excess of a given threshold;

for each tested gray-scale tissue value which does exceed the threshold, using the tested gray-scale tissue value to derive a corresponding output pixel; and for each tested gray-scale tissue value which does not exceed the threshold, deriving a flow velocity value and using the derived flow velocity value to derive the corresponding output pixel; and wherein a flow velocity value is not derived for each tested gray-scale tissue value which does exceed the threshold and for each pixel of the image plane outside the active region.

2. An ultrasound system, comprising:

an integrated circuit having a processing unit, a programmable direct memory access controller, a first memory module, and a second memory module on a common substrate; and a sequence of frames of ultrasound data derived from scanning a target area in which an n-th ultrasound data frame is followed by an n+1-th, then an n+2-th ultrasound data frame;

a display unit for displaying an image frame derived from one or more of the sequence of frames of ultrasound data;

wherein the processing unit is programmed to derive flow velocity values for any given frame of the sequence of frames;

wherein the direct memory access controller is programmed to input the ultrasound data for alternating frames in alternating memory modules of said first and second memory modules;

wherein the direct memory access controller inputs ultrasound data for the n-th frame into the first memory module;

wherein while the processing unit derives flow velocity values for the n-th frame of ultrasound data stored in the first memory module, the direct memory access controller inputs ultrasound data for the n+1-th frame into the second memory module;

wherein while the processing unit derives flow velocity values for the n+1-th frame of ultrasound data stored in the second memory module, the direct memory access controller outputs flow velocity values derived previously for the n-th frame from the first memory module, and inputs ultrasound data for the n+2-th frame of ultrasound data into the first memory module;

wherein the flow velocity values output from the first memory module are used to derive pixel data for an image frame output to the display; and wherein the sequence of frames of ultrasound data is processed and a corresponding sequence of image frames are derived and output to the display for real-time viewing of a scanned target area.

3. A method for deriving a flow velocity value for a sample point within a target area scanned by a plurality of ultrasound signals, the flow velocity value corresponding to an arc tangent of a first lag of an autocorrelation of a series of in-phase and quadrature values of ultrasound signals, the series of ultrasound signals being collected over time at the sample point, the arc tangent being of a numerator value which as an imaginary component of the first lag of the autocorrelation series and a denominator value which is a real component of the first lag of the autocorrelation series, the phase of the flow velocity value residing in one of a first quadrant, a second quadrant, a third quadrant, or a fourth quadrant, the method comprising the steps of:

where the absolute value of the numerator value is less than the absolute value of the denominator value, deriving a first index from the ratio of the absolute value of the numerator value to the absolute value of the denominator value, and using the first index to access a first look-up table having $2^x$ values and which is linearly quantized in a fixed step increment of $\frac{1}{2}^x$ to achieve a first value, wherein x is a prescribed bit precision for the look-up table values;

where the absolute value of the numerator value is greater than the absolute value of the denominator value, deriving a second index from the ratio of the absolute value of the denominator value component to the absolute value of the numerator value, and using the second index to access a second look-up table having $2^x$ values and which is nonlinearly quantized in a variable increment of $2^x/\{(2^x-u)(2^x-(u+1))\}$ to achieve the first value, where u is the u-th step increment and is not greater than $2^x$;

wherein for a non-negative numerator value and a non-negative denominator value, the first value corresponds to the flow velocity at the sample point and the phase of the flow velocity value occurs in the first quadrant;

wherein for a negative numerator value and a non-negative denominator value, the first value is transposed into the second quadrant, the transposed value corresponding to the flow velocity at the sample point and the phase of the flow velocity value occurs in the second quadrant;

wherein for a negative numerator value and a negative denominator value, the first value is transposed to the third quadrant, the transposed value corresponding to the flow velocity at the sample point and the phase of the flow velocity value occurs in the third quadrant;

wherein for a non-negative numerator value and a negative denominator value the first value is transposed to the fourth quadrant, the transposed value corresponding to the flow velocity at the sample point and the phase of the flow velocity value occurs in the fourth quadrant.

4. A method for deriving an arc tangent of a first lag of an autocorrelation of a series of in-phase and quadrature values of ultrasound signals, the series of ultrasound signals being collected over time at a common point in space, the arc tangent being of a numerator value which as an imaginary component of the first lag of the autocorrelation series and a denominator value which is a real component of the first lag of the autocorrelation series, the arc tangent occurring in one of a first quadrant, a second quadrant, a third quadrant, or a fourth quadrant, the method comprising the steps of:

where the absolute value of the numerator value is less than the absolute value of the denominator value, deriving a first index from the ratio of the absolute value of the numerator value to the absolute value of the denominator value, and using the first index to access a first look-up table having $2^x$ values and which is linearly quantized in a fixed step increment of $\frac{1}{2}^x$ to achieve a first value, wherein x is a prescribed bit precision for the look-up table values;

where the absolute value of the numerator value is greater than the absolute value of the denominator value, deriving a second index from the ratio of the absolute value of the denominator value component to the absolute value of the numerator value, and using the second index to access a second look-up table having $2^x$ values and which is nonlinearly quantized in a variable increment of $2^x/\{(2^x-u)(2^x-(u+1))\}$ to achieve the first value, where u is the u-th step increment and is not greater than $2^x$;

wherein for a non-negative numerator value and a non-negative denominator value, the first value corresponds to the derived arc tangent and occurs in the first quadrant;

wherein for a negative numerator value and a non-negative denominator value, the first value is transposed into the second quadrant, the transposed value corresponding to the derived arc tangent;

wherein for a negative numerator value and a negative denominator value, the first value is transposed to the third quadrant, the transposed value corresponding to the derived arc tangent;

wherein for a non-negative numerator value and a negative denominator value the first value is transposed to the fourth quadrant, the transposed value corresponding to the derived arc tangent.

5. A method for deriving a flow velocity value for a sample point within a target area scanned by a plurality of ultrasound signals, the flow velocity value corresponding to an arc tangent of a first lag of an autocorrelation of a series of in-phase and quadrature values of ultrasound signals, the series of ultrasound signals being collected over time at the sample point, the arc tangent being of a numerator value which as an imaginary component of the first lag of the autocorrelation series and a denominator value which is a real component of the first lag of the autocorrelation series, the phase of the flow velocity value residing in one of a first quadrant, a second quadrant, a third quadrant, or a fourth quadrant, the method comprising the steps of:

where the absolute value of the numerator value is less than the absolute value of the denominator value, deriving a first index from the ratio of the absolute value of the numerator value to the absolute value of the denominator value, and using the first index to access a first look-up table having $2^x$ values and which is linearly quantized in a fixed step increment of $\frac{1}{2}^x$ to achieve a first value, wherein x is a prescribed bit precision for the look-up table values;

where the absolute value of the numerator value is greater than the absolute value of the denominator value, deriving a second index from the ratio of the absolute value of the denominator value component to the absolute value of the numerator value, using the second index to access the first look-up table to achieve a second value, and computing pi/2 minus the second value to achieve the first value;

wherein for a non-negative numerator value and a non-negative denominator value, the first value corresponds to the flow velocity at the sample point and the phase of the flow velocity value occurs in the first quadrant;

wherein for a negative numerator value and a non-negative denominator value, the first value is transposed into the second quadrant, the transposed value corresponding to the flow velocity at the sample point and the phase of the flow velocity value occurs in the second quadrant;

wherein for a negative numerator value and a negative denominator value, the first value is transposed to the third quadrant, the transposed value corresponding to the flow velocity at the sample point and the phase of the flow velocity value occurs in the third quadrant;

wherein for a non-negative numerator value and a negative denominator value the first value is transposed to the fourth quadrant, the transposed value corresponding to the flow velocity at the sample point and the phase of the flow velocity value occurs in the fourth quadrant.

* * * * *

UNITED STATES PATENT AND TRADEMARK OFFICE
Certificate

Patent No. 5,910,117

Patented: June 8, 1999

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Christopher Basoglu, Bothell, Washington; JYongmin Kim, Seattle, Washington; Dong-Chyuan Liu, Mercer Island, Washington; and John Lazenby, Fall City, Washington.

Signed and Sealed this Seventeenth Day of July, 2001.

MARVIN LATEEF
*Supervisory Patent Examiner*
Art Unit 3737